United States Patent
Lee et al.

(10) Patent No.: US 6,835,191 B2
(45) Date of Patent: Dec. 28, 2004

(54) SELF-VENTING MOVABLE SEAL AND PLUNGER

(75) Inventors: Robert Lee, Lake Elmo, MN (US); Brian G. Koethe, Cottage Grove, MN (US); Theodore S. Swaback, Hastings, MN (US)

(73) Assignee: 3M Innovative Properties Co., St. Paul, MN (US)

( * ) Notice: Subject to any disclaimer, the term of this patent is extended or adjusted under 35 U.S.C. 154(b) by 222 days.

(21) Appl. No.: 10/028,041

(22) Filed: Dec. 21, 2001

(65) Prior Publication Data

US 2003/0120220 A1 Jun. 26, 2003

(51) Int. Cl.[7] .............................................. A61M 5/315
(52) U.S. Cl. ...................................................... 604/228
(58) Field of Search ................................ 604/122, 187, 604/200, 203, 218, 228–229, 231, 236–238, 230; 600/573, 578

(56) References Cited

U.S. PATENT DOCUMENTS

| | | | |
|---|---|---|---|
| 3,331,538 A | 7/1967 | Higgins | |
| 3,566,859 A | * 3/1971 | Schwartz | ................... 600/578 |
| 3,603,310 A | 9/1971 | Mottin et al. | |
| 4,257,426 A | * 3/1981 | Bailey | ......................... 600/579 |
| 4,299,238 A | 11/1981 | Baidwan et al. | |
| 4,615,341 A | * 10/1986 | Marzolf et al. | ............. 600/578 |
| 4,632,672 A | 12/1986 | Kvitrud | |
| 4,660,569 A | * 4/1987 | Etherington | ................. 600/578 |
| 4,934,379 A | * 6/1990 | Marzolf et al. | ............. 600/578 |
| 4,973,308 A | * 11/1990 | Borras et al. | ................ 604/110 |
| 5,176,639 A | * 1/1993 | Pozzi et al. | .................. 604/110 |
| 5,178,305 A | 1/1993 | Keller | |
| 5,865,803 A | 2/1999 | Major | |
| 6,228,065 B1 | 5/2001 | Lynn | |
| 6,235,002 B1 | 5/2001 | Carver, Jr. et al. | |

FOREIGN PATENT DOCUMENTS

| | | |
|---|---|---|
| DE | 29617949 U1 | 6/1997 |
| WO | WO 01/91836 | 12/2001 |

* cited by examiner

*Primary Examiner*—LoAn H. Thanh
(74) *Attorney, Agent, or Firm*—Sean Edman

(57) ABSTRACT

A self-venting movable seal and plunger assembly for use in dispensing materials from cylindrical bodies is disclosed. The assembly includes a self-venting movable seal and a plunger tip that seats within a plunger tip pocket in the movable seal, occluding a vent in the movable seal. Methods of using the assembly to dispense materials are also disclosed.

23 Claims, 5 Drawing Sheets

SELF-VENTING MOVABLE SEAL AND PLUNGER

FIELD OF THE INVENTION

The present invention relates to the field of syringes, more particularly, syringe plungers.

BACKGROUND

Syringes typically include a barrel forming a hollow cylindrical body and a plunger located within the hollow cylindrical body. The plunger typically seals against the inner surface of the hollow cylindrical body. As a result, movement of the plunger within the hollow cylindrical body can be used to fill and/or dispense materials using the syringe.

A problem exists in removing air from between the plunger and material (e.g., a liquid or paste) within the barrel when the syringe is loaded with the material at a factory or by a user. For example, dispensing air with the material may make it difficult to accurately dispense a precise dosage, especially when the dosages are very small. Further, syringes that have trapped, compressed air tend to dispense material after pressure on the plunger is released due to the compressed air, resulting in weeping or oozing of the material.

Various plunger structures have been developed to vent this air when the plunger is inserted into the syringe barrel. Many of these structures do not, however, work well with materials having low viscosity because the structures allow the material to vent through the plunger away from the dispensing end of the syringe barrel. As a result, users have resorted to filling syringes under vacuum conditions, which is both expensive and time consuming. Further, some plunger structures only seal when pressure is applied to the plunger in the forward direction. Thus, air can be drawn back into the syringe barrel if movement of the plunger is reversed during use.

SUMMARY OF THE INVENTION

The present invention provides a self-venting movable seal and plunger assembly. The present invention also provides methods of using the assembly to dispense material. The assembly includes a movable seal and a plunger tip that allows the removal of an unwanted fluid from a cylindrical dispenser, e.g., syringe.

Among the advantages provided by the present invention is the ability to remove unwanted fluid from a cylindrical dispenser that is trapped between the material to be dispensed and the seal. The assembly can either be preassembled in the hollow cylindrical body and later filled by the user, or the user can first fill the body with the material and then insert the assembly into the hollow cylindrical body.

In one aspect, the present invention provides a method for venting trapped fluid out of a hollow cylindrical body while the hollow cylindrical body is being filled with a material by providing a hollow cylindrical body including a first opening and a second opening; a seal including a vent and a plunger tip pocket; and a plunger tip including at least one vent channel. The method further includes inserting the seal into the hollow cylindrical body, wherein a volume is defined within the hollow cylindrical body between the seal and the second opening of the hollow cylindrical body, and further wherein the volume contains a fluid. The method further includes filling the hollow cylindrical body with the material through the second opening of the hollow cylindrical body, wherein the fluid within the volume is vented through the vent of the seal as the material occupies the volume; inserting the plunger tip into the hollow cylindrical body via the first opening of the hollow cylindrical body; and seating the plunger tip in the plunger tip pocket of the seal, wherein the plunger tip occludes the vent when the plunger tip is seated in the plunger tip pocket, and further wherein fluid within the plunger tip pocket escapes through the at least one vent channel in the plunger tip while the plunger tip is being seated in the plunger tip pocket.

In another aspect, the present invention provides a method for venting trapped fluid out of a hollow cylindrical body while the hollow cylindrical body is being filled with a material by providing a hollow cylindrical body including a first opening and a second opening; a seal including a vent and a plunger tip pocket; and a plunger tip including at least one vent channel. The method further includes filling the hollow cylindrical body with the material; inserting the seal into the hollow cylindrical body, wherein a volume is defined within the hollow cylindrical body between the seal and the second opening of the hollow cylindrical body, wherein the volume contains a fluid, and further wherein the fluid within the volume is vented through the vent of the seal as the seal is inserted into the hollow cylindrical body. The method further includes inserting the plunger tip into the hollow cylindrical body through the first opening of the hollow cylindrical body; and seating the plunger tip into the plunger tip pocket of the seal, wherein the plunger tip occludes the vent when the plunger tip is seated in the plunger tip pocket, and further wherein fluid within the plunger tip pocket escapes through the at least one vent channel in the plunger tip while the plunger tip is being seated in the plunger tip pocket.

In another aspect, the present invention provides a self-venting movable seal and plunger assembly that includes a hollow cylindrical body including a first opening and a second opening; a movable seal including a plunger tip pocket, a first end and a second end, wherein a volume is defined within the hollow cylindrical body between the second end of the seal and the second opening of the hollow cylindrical body when the movable seal is located within the hollow cylindrical body, and a vent extending between the plunger tip pocket and the second end of the movable seal, wherein the plunger tip pocket is in fluid communication with the volume when the movable seal is located within the hollow cylindrical body; and a plunger tip including at least one vent channel, wherein the plunger tip is configured to seat within the plunger tip pocket of the movable seal, wherein the plunger tip occludes the vent in the movable seal when the plunger tip is seated within the plunger tip pocket, and further wherein fluid within the plunger tip pocket escapes through the at least one vent channel in the plunger tip as the plunger tip is seated in the plunger tip pocket.

In another aspect, the present inventions provides a self-venting movable seal and plunger assembly including a hollow cylindrical body including a first opening and a second opening; a movable seal including a plunger tip pocket, a first end and a second end, wherein a volume is defined within the hollow cylindrical body between the second end of the seal and the second opening of the hollow cylindrical body when the movable seal is located within the hollow cylindrical body, a vent extending between the plunger tip pocket and the second end of the movable seal, wherein the plunger tip pocket is in fluid communication with the volume when the movable seal is located within the hollow cylindrical body, and at least one pair of retaining plug receptacles; and a plunger tip including at least one vent channel, and at least one pair of retaining plugs, wherein the plunger tip is configured to seat within the plunger tip pocket of the movable seal, wherein the plunger tip occludes the vent in the movable seal when the plunger tip is seated within the plunger tip pocket, wherein fluid within the plunger tip pocket escapes through the at least one vent channel in the plunger tip as the plunger tip is seated in the plunger tip pocket, and further wherein the at least one pair of retaining plugs is configured to fit in the at least one pair of retaining plug receptacles of the movable seal.

These and other features and advantages of the invention may be described in more detail below in connection with some illustrative embodiments of the invention.

BRIEF DESCRIPTION OF THE DRAWINGS

FIG. 1C is a side view of the plunger tip of FIG. 1A.

DETAILED DESCRIPTION OF ILLUSTRATIVE EMBODIMENTS OF THE INVENTION

The present invention provides a self-venting movable seal and plunger that is capable of venting trapped fluid out of a hollow cylindrical body and methods for using same.

As used herein, the term "material" is used to encompass any material that may be dispensed from a dispenser, e.g., syringe, etc. It may be preferred that the materials used include sealants, adhesives, or etchants.

The term "fluid" as used herein includes any unwanted fluid that may be trapped between the seal of the present invention and the material to be dispensed from the hollow cylindrical body, including, e.g., gasses, such as air, and low-viscosity liquids, such as water.

Figure 1A:
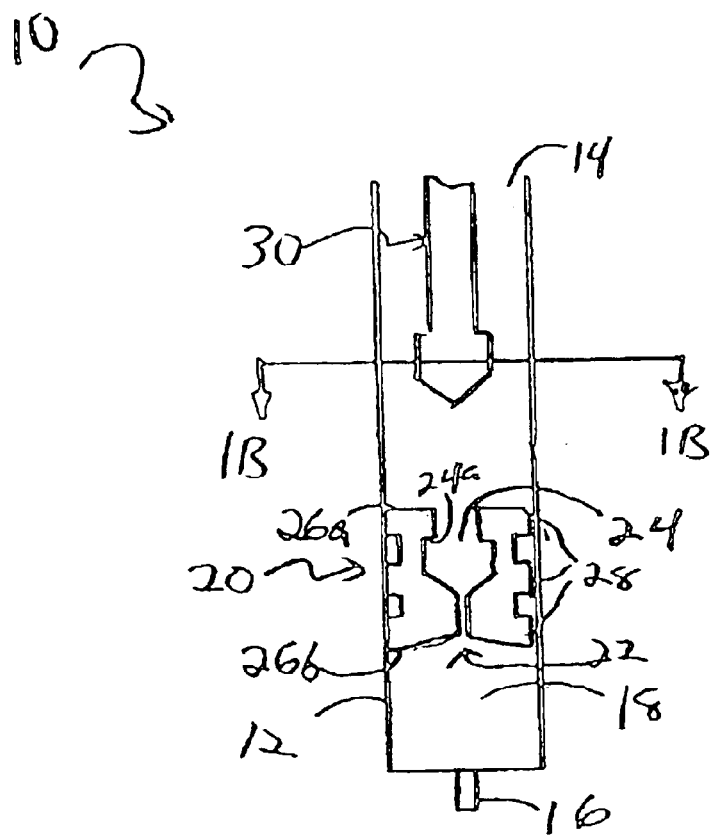
FIG. 1A is a cross-section view of one self-venting movable seal and plunger assembly of the present invention.
Figure 1B:
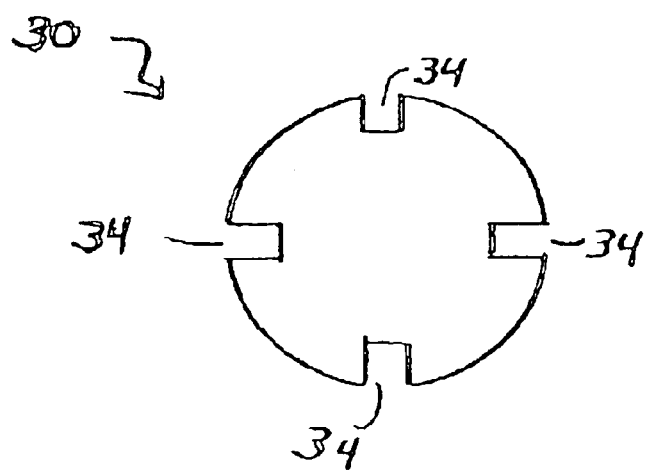
FIG. 1B is a cross-section of the plunger tip of FIG. 1A taken along line 1B.

FIGS. 1A–1C depict one illustrative embodiment of a self-venting movable seal and plunger assembly 10 according to the present invention. The assembly 10 includes a hollow cylindrical body 12 that receives a movable seal 20 and plunger tip 30. The hollow cylindrical body 12 may be, e.g., the barrel of a syringe.

Although generally a circular cylinder, the hollow cylindrical body 12 may take any suitable cross-sectional shape that allows for material to be dispensed therefrom, e.g., octagonal, square, elliptical, etc.

The hollow cylindrical body 12 includes a first opening 14 and a second opening 16. The first opening 14 is preferably configured to allow insertion of the movable seal 20, whereas the second opening 16 is configured to allow material to be dispensed from the hollow cylindrical body 12. The second opening 16 may be any suitable diameter depending on, e.g., the viscosity of the material to be dispensed, the desired quantity of material dispensed, etc. The hollow cylindrical body 12 may be manufactured using any suitable material or materials known in the art, e.g., polymeric, glass, metal, etc.

Located within the hollow cylindrical body 12 is a movable seal 20. The movable seal 20 includes a vent 22, a plunger tip pocket 24, and at least one annular seal ring 28 (the depicted seal 20 includes three seal rings 28). The seal 20 further includes a first end 26a and a second end 26b. The first end 26a may take any profile, while the second end 26b may preferably be concave in shape. A concave second end 26b may more easily allow trapped fluid to escape through vent 22 when the cylindrical body 12 is held upright as depicted in FIG. 1A. Any suitable material or materials known in the art may be used to manufacture the seal 20, e.g., rubber, polymeric material, etc.

A volume 18 is defined within the hollow cylindrical body 12 between the movable seal 20 and the second opening 16 of the hollow cylindrical body 12.

The vent 22 is preferably located approximately in the center of the second end 26b of the seal 20 and may be sized in accordance with the characteristics of the material to be dispensed. For example, higher viscosity materials may allow for a larger diameter vent 22, while lower viscosity materials may require a smaller diameter vent 22. It may be preferred that the vent 22 has, e.g., a diameter of 0.01 to 0.02 cm for low viscosity materials.

Further, the vent 22 may have any shape that allows fluid to vent from the second end 26b of the seal to the first end 26a. For example, the vent 22 may be straight as depicted in FIG. 1A, or the vent 22 may follow a more tortuous path to allow fluid to vent while resisting the escape of material to be dispensed. Although depicted as a single vent 22, the seal 20 of the present invention may include a plurality of vents for venting fluid from the second end 26b to the first end 26a of the seal 20.

The seal 20 may also include a plunger tip pocket 24 that is configured to receive a plunger tip 30. The plunger tip pocket 24 may include a lip 24a that allows the plunger tip 30 to lock into or mechanically engage with the plunger tip pocket 24 when the plunger tip 30 is seated in the plunger tip pocket 24. The plunger tip pocket 24 may be any shape that can receive and seat the plunger tip 30.

Located around an outside surface of the seal 20 is at least one annular seal ring 28. Although depicted in FIG. 1A as having three rings, the seal 20 may have any number of annular seal rings 28. The annular seal rings 28 may be sized such that they have a slighter greater diameter than the hollow cylindrical body 12 so that the seal 20 seals the material to be dispensed within the hollow cylindrical body 12. It may be preferred that the seal 20 include a plurality of annular seal rings 28 such that the overall friction between the hollow cylindrical body 12 and the seal 20 is reduced while still maintaining a desired seal.

The assembly 10 of the present invention further includes a plunger tip 30 that is configured to fit within the plunger tip pocket 24 of the seal 20. The plunger tip 30 includes at least one vent channel 34, as depicted in FIGS. 1B and 1C. The at least one vent channel 34 allows fluid that may be trapped in the plunger tip pocket 24 to escape while the plunger tip 30 is being seated in the plunger tip pocket 24. Further, the plunger tip 30 may be used to move the seal 20 toward the material to be dispensed. Although any suitable shape of plunger tip 30 may be used, it may be preferred that the plunger tip 30 is shaped such that it locks into or mechanically engages with the plunger tip pocket 24. When seated, the plunger tip 30 occludes the vent 22 such that material does not vent through the plunger tip pocket 24 while the material is being dispensed.

The plunger tip 30 may be manufactured of any suitable material or materials known in the art, e.g., rubber, polymeric, etc. Further, the plunger tip 30 may be connected to a handle (not shown) that could allow a user to seat the plunger tip 30 in the plunger tip pocket 24 and apply a dispensing force to the assembly 10 such that material is dispensed through the second opening 16 of the hollow cylindrical body 12.

Figure 2C:
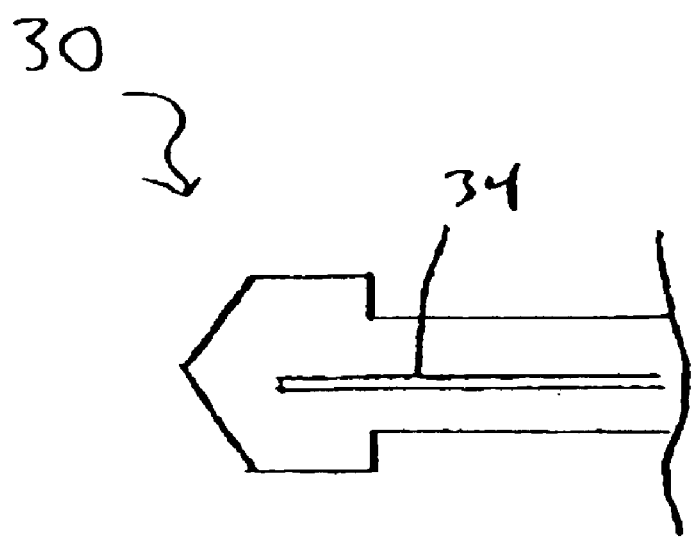
FIG. 2 is a cross-section view of an alternative embodiment of the present invention.
Figure 2:
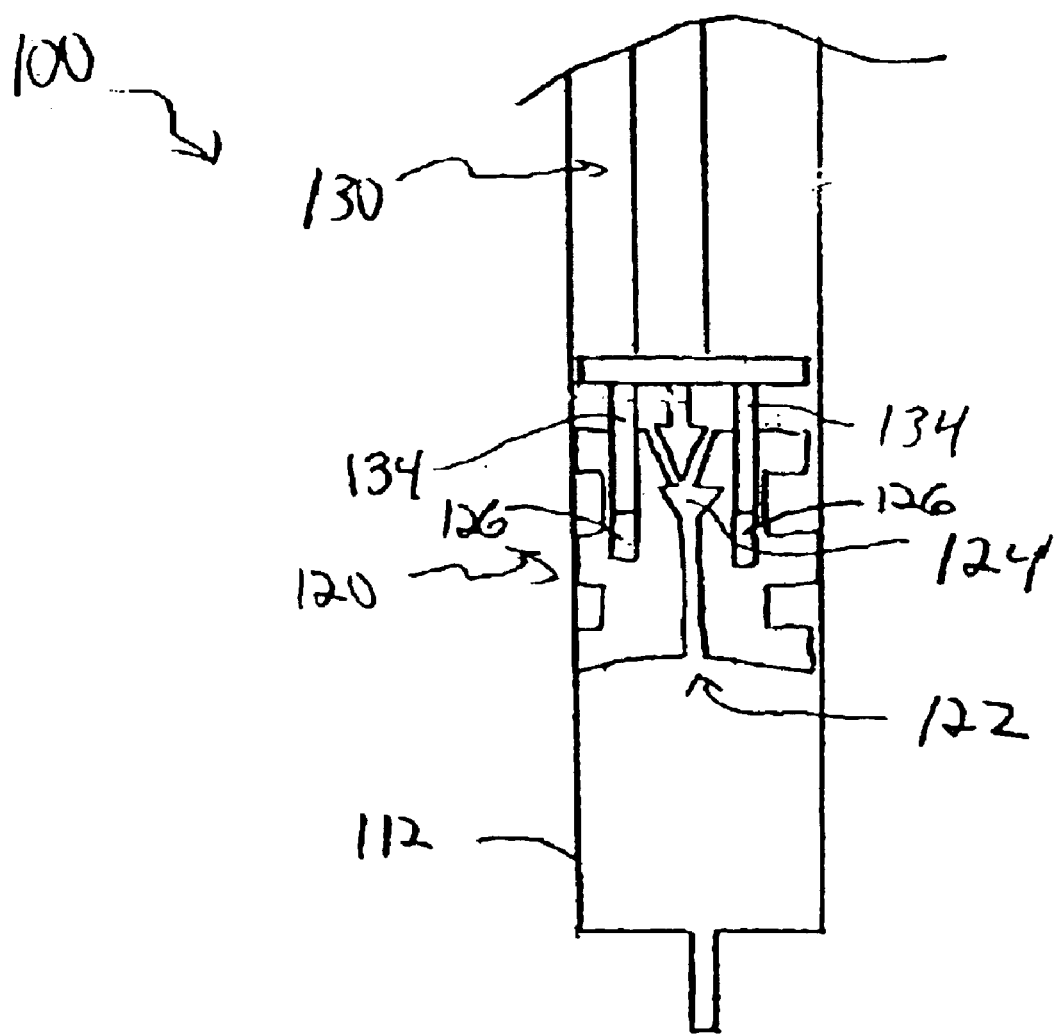

FIG. 2 depicts another embodiment of a self-venting movable seal and plunger assembly 100 according to the present invention. In many respects, the assembly 100 is similar to the assembly 10 of FIGS. 1A–1C. The assembly 100 includes a hollow cylindrical body 112, a movable seal 120, and a plunger tip 130. The plunger tip 130 is designed to be seated within a plunger tip pocket 124 of the seal 120 and occlude a vent 122 in the seal 120.

Among the differences between the assembly 100 and the assembly 10 of FIGS. 1A–1C are at least one pair of retaining plug receptacles 126 and at least one pair of retaining plugs 134. As depicted in FIG. 2, the seal 120 includes at least one pair of retaining plug receptacles 126 that are configured to receive the at least one pair of retaining plugs 134 that are included in the plunger tip 130. The at least one pair of retaining plugs 134 are configured such that the plunger tip 130 may be attached to the seal 120 prior to completely seating the plunger tip 130 in the plunger tip pocket 124 without requiring engagement of the plunger tip 130 in plunger tip pocket 124. It may be preferred that the at least one pair of retaining plugs 134 are configured such that friction is created upon insertion into the at least one pair of retaining plug receptacles 126, although any suitable method of attachment may be used. Further, the at least one pair of retaining plugs 134 and the at least one pair of retaining plug receptacles 126 are only one example of a structure for retaining the seal 120 in connection with the plunger tip 130.

The at least one pair of retaining plugs 134 and the at least one pair of retaining plug receptacles 126 may allow the plunger tip 130 to be preassembled with the seal 120 while leaving the vent 122 open. When material is to be dispensed, the plunger tip 130 is completely seated in the plunger tip pocket 124 such that the plunger tip 130 occludes the vent 122, thus preventing material from being vented through the seal 120. Further, the plunger tip 130 may lock into or mechanically engage with the movable seal 120 upon dispensing the material.

Figure 3A:
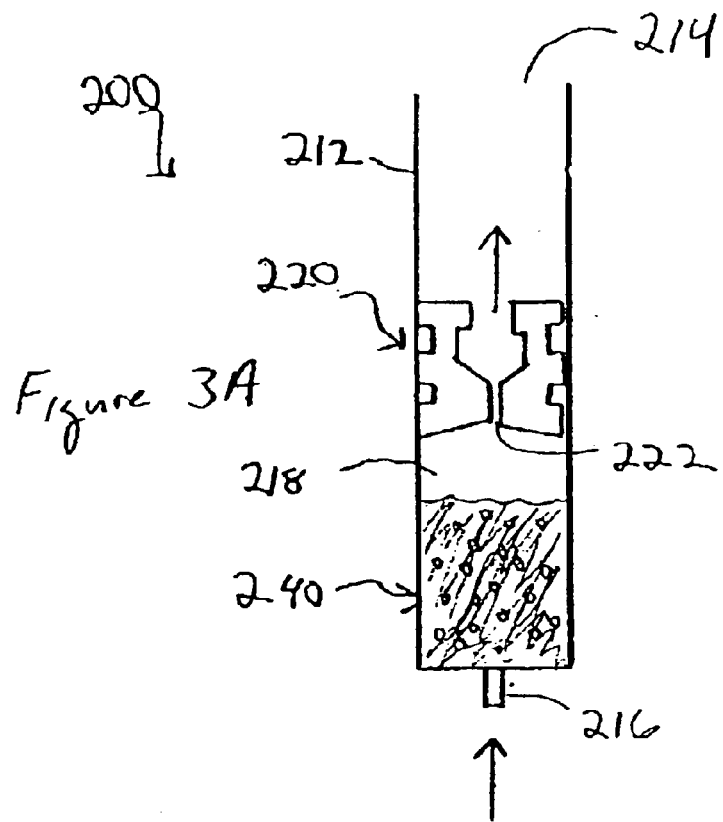
FIGS. 3A–3B illustrate use of a self-venting movable seal and plunger assembly of the present invention.
Figure 3B:
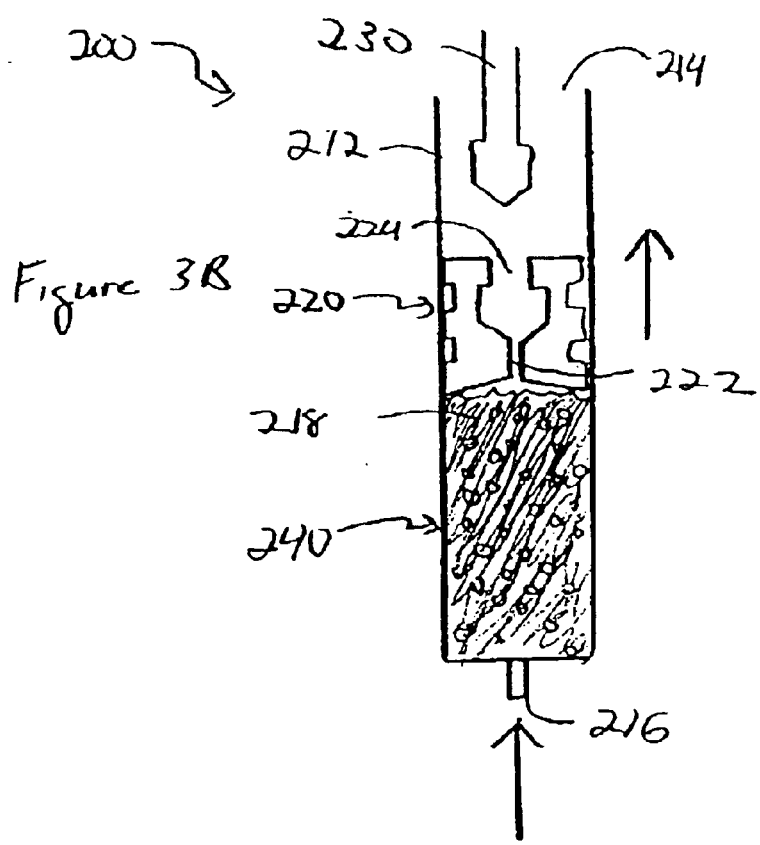

One method of venting trapped fluid out of a hollow cylindrical body while the hollow cylindrical body is being filled using the assembly of the present invention can be described in reference to FIGS. 3A–3B. A self-venting movable seal and plunger assembly 200 is provided as described above, including a hollow cylindrical body 212, and a seal 220. The assembly 200 is employed by inserting the seal 220 into the hollow cylindrical body 212 through the first opening 214 of the hollow cylindrical body 212.

The assembly 200 is then prepared by filling the hollow cylindrical body 212 with a material 240 to be dispensed via the second opening 216 of the hollow cylindrical body 212. The material 240 and seal 220 may define a volume 218 between them within the body 212. As the material 240 moves up the hollow cylindrical body 212 toward the first opening 214, fluid that is located in volume 218 escapes through the vent 222 of the seal 220 as the material 240 occupies volume 218.

If the seal 220 is low enough such that the volume 218 is too small for the desired amount of material 240 to be dispensed, then the material 240 may move the seal 220 away from the second opening 216 toward the first opening 214 of the hollow cylindrical body 212, as is depicted in FIG. 3B. In such a situation, it may be preferred that the vent 222 be sized or configured to prevent or minimize passage of the material 240 through the vent 222 as the seal 220 is moved within the body 212 by the material 240.

The plunger tip 230 may then be inserted into the plunger tip pocket 224 of the seal 220. Back pressure of the material 240 and the vent 222 may allow the plunger tip 230 to be introduced into the plunger tip pocket 224 without causing material 240 to leak out the seal vent 222. The force required to seat the plunger tip 230 into the plunger tip pocket 224 is preferably less than the force required to pass the material 240 through the vent 222. When seated in the plunger tip pocket 224, the plunger tip 230 occludes the vent 222, thus preventing material 240 from being vented through the vent 222 into the plunger tip pocket 224.

When seated, the plunger tip 230 may lock into or mechanically engage with the plunger tip pocket 224 such that the plunger tip 230 and seal 220 are attached for movement in either direction within the body 212. This may allow for the seal 220 to be retracted by the user. When the seal 220 is retracted, negative pressure may be created in volume 218.

Figure 4:
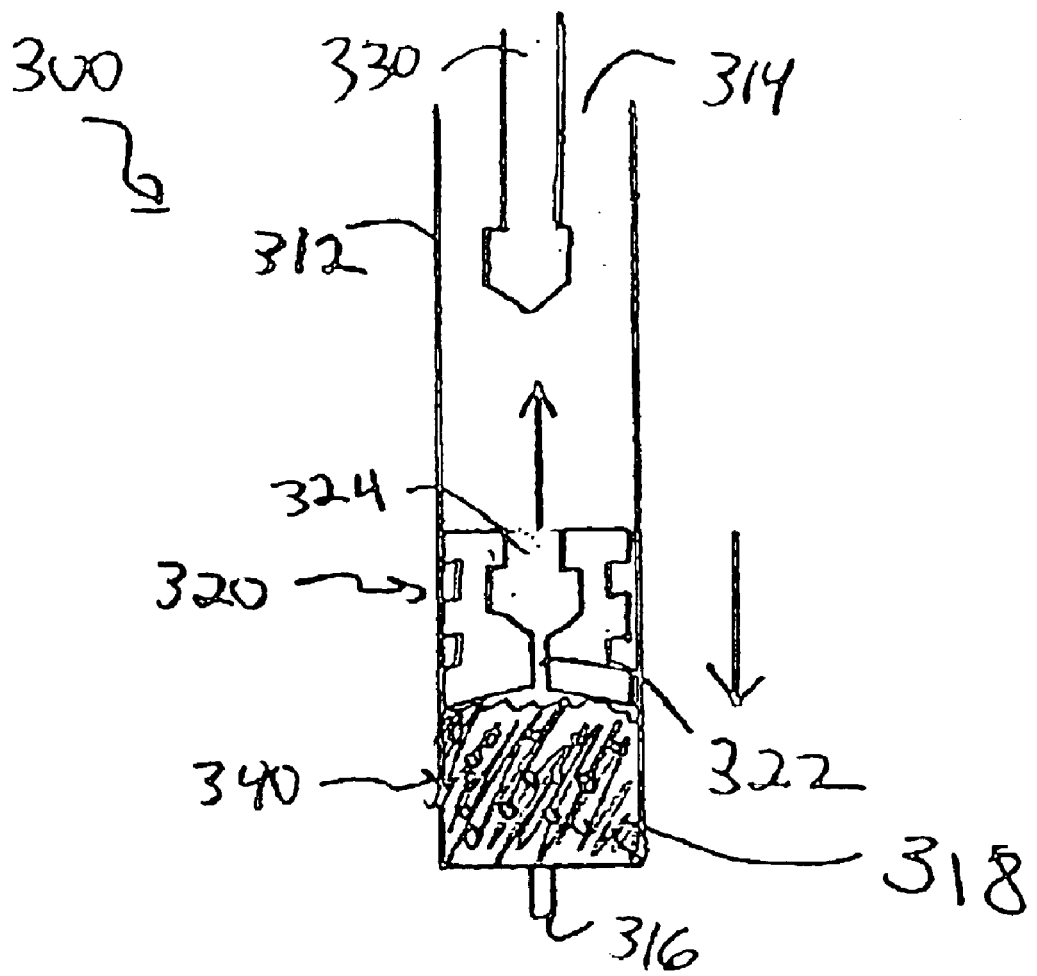
FIG. 4 illustrates another use of a self-venting movable seal and plunger assembly of the present invention.

An alternative method of venting trapped fluid out of a hollow cylindrical body while the hollow cylindrical body is being filled with a material is also described in reference to FIG. 4. Here, the hollow cylindrical body 312 is prepared by first filling the hollow cylindrical body 312 with material 340 to be dispensed.

The seal 320 is then inserted into the hollow cylindrical body 312 via the first opening 314, thus defining volume 318 between the seal 320 and the second opening 316 of the hollow cylindrical body 312. Any fluid located in volume 318 is vented through the vent 322 of the seal 320 as the seal 320 is inserted into the hollow cylindrical body 312 and advanced toward the material 340.

The plunger tip 330 may then be seated in the hollow cylindrical body 312 via the first opening 314 and seated in the plunger tip pocket 324 of the seal 320. When seated, the plunger tip 330 occludes the vent 322, thus preventing material 340 from being vented through vent 322 into the plunger tip pocket. When seated, the plunger tip 330 may lock into or mechanically engage with the plunger tip pocket 324 as described above.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of this invention, and it should be understood that this invention is not limited to the illustrative embodiments set forth herein. Accordingly, the invention is to be limited only by the claims provided below.

What is claimed is:

1. A method for venting trapped fluid out of a hollow cylindrical body while the hollow cylindrical body is being filled with a material, the method comprising:

providing a hollow cylindrical body comprising a first opening and a second opening;

providing a seal comprising a vent and a plunger tip pocket;

providing a plunger tip comprising at least one vent channel;

inserting the seal into the hollow cylindrical body, wherein a volume is defined within the hollow cylindrical body between the seal and the second opening of the hollow cylindrical body, and further wherein the volume contains a fluid;

filling the hollow cylindrical body with the material through the second opening of the hollow cylindrical body, wherein the fluid within the volume is vented through the vent of the seal as the material occupies the volume;

inserting the plunger tip into the hollow cylindrical body via the first opening of the hollow cylindrical body; and seating the plunger tip in the plunger tip pocket of the seal, wherein the plunger tip occludes the vent when the plunger tip is seated in the plunger tip pocket, and further wherein fluid within the plunger tip pocket escapes through the at least one vent channel in the plunger tip while the plunger tip is being seated in the plunger tip pocket.

2. The method of claim 1, wherein the plunger tip locks into the plunger tip pocket of the seal when the plunger tip is seated in the plunger tip pocket.

3. The method of claim 2, further comprising retracting the plunger tip and the seal, whereby negative pressure is created in the volume.

4. The method of claim 1, wherein the seal further comprises a concave surface adjacent the volume.

5. The method of claim 4, wherein the vent is located proximate a center of the concave surface of the seal.

6. The method of claim 1, wherein the seal further comprises at least one pair of retaining plug receptacles, and further wherein the plunger tip further comprises at least one pair of retaining plugs.

7. The method of claim 6, wherein seating the plunger tip in the plunger tip pocket of the seal further comprises inserting the at least one pair of retaining plugs of the plunger tip in the at least one pair of retaining plug receptacles of the seal.

8. A method for venting trapped fluid out of a hollow cylindrical body while the hollow cylindrical body is being filled with a material, the method comprising:

providing a hollow cylindrical body comprising a first opening and a second opening;

providing a seal comprising a vent and a plunger tip pocket;

providing a plunger tip comprising at least one vent channel;

filling the hollow cylindrical body with the material;

inserting the seal into the hollow cylindrical body, wherein a volume is defined within the hollow cylindrical body between the seal and the second opening of the hollow cylindrical body, wherein the volume contains a fluid, and further wherein the fluid within the volume is vented through the vent of the seal as the seal is inserted into the hollow cylindrical body;

inserting the plunger tip into the hollow cylindrical body through the first opening of the hollow cylindrical body; and seating the plunger tip into the plunger tip pocket of the seal, wherein the plunger tip occludes the vent when the plunger tip is seated in the plunger tip pocket, and further wherein fluid within the plunger tip pocket escapes through the at least one vent channel in the plunger tip while the plunger tip is being seated in the plunger tip pocket.

9. The method of claim 8, wherein the plunger tip locks into the plunger tip pocket of the seal when the plunger tip is seated in the plunger tip pocket.

10. The method of claim 9, further comprising retracting the plunger tip and the seal, whereby negative pressure is created in the volume.

11. The method of claim 8, wherein the seal further comprises a concave surface adjacent the volume.

12. The method of claim 11, wherein the vent is located proximate a center of the concave surface of the seal.

13. The method of claim 8, wherein the seal further comprises at least one pair of retaining plug receptacles, and further wherein the plunger tip further comprises at least one pair of retaining plugs.

14. The method of claim 13, wherein seating the plunger tip in the plunger tip pocket of the seal further comprises inserting the at least one pair of retaining plugs of the plunger tip in the at least one pair of retaining plug receptacles of the seal.

15. A self-venting movable seal and plunger assembly, the assembly comprising:

a hollow cylindrical body comprising a first opening and a second opening;

a movable seal comprising:
  a plunger tip pocket,
  a first end and a second end, wherein a volume is defined within the hollow cylindrical body between the second end of the seal and the second opening of the hollow cylindrical body when the movable seal is located within the hollow cylindrical body, and
  a vent extending between the plunger tip pocket and the second end of the movable seal, wherein the plunger tip pocket is in fluid communication with the volume when the movable seal is located within the hollow cylindrical body; and a plunger tip comprising at least one vent channel, wherein the plunger tip is configured to seat within the plunger tip pocket of the movable seal, wherein the plunger tip occludes the vent in the movable seal when the plunger tip is seated within the plunger tip pocket, and further wherein fluid within the plunger tip pocket escapes through the at least one vent channel in the plunger tip as the plunger tip is seated in the plunger tip pocket.

16. The assembly of claim 15, wherein the plunger tip is configured to lock into the plunger tip pocket of the seal.

17. The assembly of claim 15, wherein the seal further comprises at least one pair of retaining plug receptacles, and further wherein the plunger tip further comprises at least one pair of retaining plugs configured to fit in the at least one pair of retaining plug receptacles of the seal.

18. The assembly of claim 15, wherein the second end of the seal comprises a concave surface.

19. The assembly of claim 18, wherein the vent is located proximate a center of the concave surface of the first end of the seal.

20. A self-venting movable seal and plunger assembly, the assembly comprising:

a hollow cylindrical body comprising a first opening and a second opening;

a movable seal comprising:
  a plunger tip pocket,
  a first end and a second end, wherein a volume is defined within the hollow cylindrical body between the second end of the seal and the second opening of the hollow cylindrical body when the movable seal is located within the hollow cylindrical body,
  a vent extending between the plunger tip pocket and the second end of the movable seal, wherein the plunger tip pocket is in fluid communication with the volume when the movable seal is located within the hollow cylindrical body, and at least one pair of retaining plug receptacles; and a plunger tip comprising:

at least one vent channel, and at least one pair of retaining plugs, wherein the plunger tip is configured to seat within the plunger tip pocket of the movable seal, wherein the plunger tip occludes the vent in the movable seal when the plunger tip is seated within the plunger tip pocket, wherein fluid within the plunger tip pocket escapes through the at least one vent channel in the plunger tip as the plunger tip is seated in the plunger tip pocket, and further wherein the at least one pair of retaining plugs is configured to fit in the at least one pair of retaining plug receptacles of the movable seal.

21. The assembly of claim 20, wherein the plunger tip is configured to lock into the plunger tip pocket of the seal.

22. The assembly of claim 20, wherein the second end of the seal comprises a concave surface.

23. The assembly of claim 22, wherein the vent is located proximate a center of the concave surface of the first end of the seal.

* * * * *